United States Patent [19]

Stern et al.

[11] Patent Number: 5,451,702
[45] Date of Patent: Sep. 19, 1995

[54] PROCESS FOR PREPARING SUBSTITUTED AROMATIC AMINES

[75] Inventors: Michael K. Stern, University City; Brian K-M Cheng, St. Charles, both of Mo.

[73] Assignee: Monsanto Company, St. Louis, Mo.

[21] Appl. No.: 51,964

[22] Filed: Apr. 26, 1993

[51] Int. Cl.$^6$ ............................................. C07C 209/22
[52] U.S. Cl. ...................... 564/415; 534/588; 534/856; 534/869; 564/395; 564/409; 564/414; 564/420; 564/421; 564/422; 564/423; 564/434; 564/435
[58] Field of Search ............... 564/394, 395, 414, 415, 564/409

[56] References Cited

U.S. PATENT DOCUMENTS

| | | | |
|---|---|---|---|
| 2,822,395 | 2/1958 | Dent | 564/392 |
| 3,340,302 | 9/1967 | Young | 564/402 |
| 3,847,990 | 11/1974 | Blahak | 564/393 |
| 4,122,118 | 10/1978 | George et al. | 564/406 |
| 4,140,716 | 2/1979 | Maender et al. | 564/132 |
| 4,155,936 | 5/1979 | Sturm | 564/406 |
| 4,187,248 | 2/1980 | Merten et al. | 564/414 |
| 4,187,249 | 2/1980 | Merten et al. | 564/414 |
| 4,187,315 | 12/1980 | Zengel et al. | 514/529 |
| 4,196,146 | 4/1980 | Merten et al. | 564/414 |
| 4,209,463 | 6/1980 | Maender et al. | 564/406 |
| 4,404,401 | 9/1983 | Zengel et al. | 564/416 |
| 4,479,008 | 10/1984 | Batorewicz et al. | 564/443 |
| 4,518,803 | 5/1985 | Batorewicz et al. | 564/410 |

(List continued on next page.)

FOREIGN PATENT DOCUMENTS 1036262  8/1954  Germany .
 770299  3/1957  United Kingdom .
1440767  6/1976  United Kingdom .

(List continued on next page.)

OTHER PUBLICATIONS

Ayyangar, N. R. et al., "A Novel Reaction of Acetanilide with Nitrobenzene in DMSO—An Unusual Solvent Assisted Regioselective Aromatic Nucleophilic Substitution", *Tetrahedron Letters,* vol. 31, No. 22, pp. 3217–3220 (1990).

(List continued on next page.)

*Primary Examiner*—Gary E. Hollinden
*Assistant Examiner*—B. Burn
*Attorney, Agent, or Firm*—Kenneth D. Goetz; Paul L. Passley; James C. Bolding

[57] ABSTRACT

A process for preparing substituted aromatic amines is provided which comprises contacting a nucleophilic compound and an azo containing compound in the presence of a suitable solvent system, reacting the nucleophilic compound and the azo containing compound in the presence of a suitable base and a controlled amount of protic material at a temperature of about 10° C. to about 150° C. in a confined reaction zone wherein the molar ratio of protic material to base is 0:1 to about 5:1 and reducing the product of the reaction of the nucleophilic compound and the azo containing compound under conditions which produce the substituted aromatic amine. In another embodiment, the substituted aromatic amines of the invention are reductively alkylated to produce alkylated diamines or substituted derivatives thereof. In another embodiment, a process for preparing alkylated aromatic amines or substituted derivatives thereof is provided which comprises contacting a nucleophilic compound and an azo containing compound in the presence of a suitable solvent system, reacting the nucleophilic compound and the azo containing compound in the presence of a suitable base and a controlled amount of protic material at a temperature of about 10° C. to about 150° C. in a confined reaction zone wherein the molar ratio of protic material to base is 0:1 to about 5:1, and reductively alkylating the product of the reaction of nucleophilic compound and the azo containing compound under conditions which produce the alkylated aromatic amine or substituted derivative thereof.

77 Claims, No Drawings

U.S. PATENT DOCUMENTS

| | | | |
|---|---|---|---|
| 4,614,817 | 9/1986 | Maender et al. | 564/406 |
| 4,670,595 | 6/1987 | Podder | 564/406 |
| 4,683,332 | 7/1987 | Sturm | 564/414 |
| 4,760,186 | 7/1988 | Solodar | 564/415 |
| 4,900,868 | 2/1990 | Merten et al. | 564/398 |

FOREIGN PATENT DOCUMENTS

| | | |
|---|---|---|
| WO-A-9300324 | 1/1993 | WIPO . |
| WO-A-9324450 | 12/1993 | WIPO . |

OTHER PUBLICATIONS

Wohl, A., "Toward the Knowledge of the Reaction Between Nitrobenzene and Aniline in the Presence of Alkali", *Chemische Berichte*, 36, pp. 4135–4138 (1903).

Wohl, A. and Aue, W., *Chemische Berichte*, 34, pp. 2442–2450 (1901).

Jencks, W. P., *J. Am. Chem. Soc.*, 92, 3201–3202 (1970).

Jeon, S. and Sawyer, D. T., "Hydroxide–Induced Synthesis of the Superoxide Ion from Dioxygen and Aniline, Hydroxlamine, or Hydrazine", *Inorg. Chem.*, 29, 4612–4615 (1990).

Bentley, T. W., "Electrochemical Oxiditative Substitution and Dimerization of 1–arylazo–2–naphthols, Leading to a New Synthesis of Some Unsymmetrical Diarylamines", *Tetrahedron Letters*, vol. 27 No. 43, pp. 5261–5264 (1986).

Newbold, B. T., "Reduction and synthetic uses of hydrazo, azo and azoxy compounds", The chemistry of the hydrazo, azo and azoxy groups—Part 2, Chap. 15—pp. 599–641, S. Patai ed., John Wiley & Sons (1975).

Rerick, M. N., "the Chemistry of the Mixed Hydrides", Reduction—Techniques and Applications in Organic Synthesis, Chap. 1—pp. 76–77, R. L. Augustine ed., Marcel Dekker, Inc. (1968).

Smith, M., "Dissolving Metal Reductions", Reduction—Techniques and Applications in Organic Synthesis, Chap. 2—pp. 147 and 155, R. R. Augustine ed., Marcel Dekker, Inc. (1968).

Rondestvedt, C. S., "Synthesis of 4–Aminodiphenylamine and Its Relatives", *J. Org. Chem.*, 42 (10), 1786–90 (1977).

und 5,451,702

PROCESS FOR PREPARING SUBSTITUTED AROMATIC AMINES

BACKGROUND OF THE INVENTION

This invention relates to the production of substituted aromatic amines. In another aspect, this invention relates to the production of 4-aminodiphenylamine (4-ADPA) or substituted derivatives thereof. In another aspect, this invention relates to the preparation of alkylated aromatic amines or substituted derivatives thereof useful as antioxidants from the substituted aromatic amines, such as 4-ADPA or substituted derivatives thereof.

It is known to prepare substituted aromatic amines by way of a nucleophilic aromatic substitution mechanism wherein an amino functional nucleophile replaces halide. For example, it is known to prepare 4-ADPA by way of a nucleophilic aromatic substitution mechanism, wherein an aniline derivative replaces halide. This method involves preparation of a 4-ADPA intermediate, namely 4-nitrodiphenylamine (4-NDPA) followed by reduction of the nitro moiety. The 4-NDPA is prepared by reacting p-chloronitrobenzene with an aniline derivative, such as formanilide or an alkali metal salt thereof, in the presence of an acid acceptor or neutralizing agent, such as potassium carbonate, and, optionally, utilizing a catalyst. See, for example, U.S. Pat. Nos. 4,187,248; 4,683,332; 4,155,936; 4,670,595; 4,122,118; 4,614,817; 4,209,463; 4,196,146; 4,187,249; 4,140,716. This method is disadvantageous in that the halide that is displaced is corrosive to the reactors and appears in the waste stream and must therefore be disposed of at considerable expense. Furthermore, use of an aniline derivative such as formanilide, and use of p-chloro-nitrobenzene, requires additional manufacturing equipment and capabilities to produce such starting materials from aniline and nitrobenzene, respectively.

It is also known to prepare 4-ADPA from the head-to-tail coupling of aniline. See, for example, G.B. 1,440,767 and U.S. Pat. No. 4,760,186. This method is disadvantageous in that the yield of 4-ADPA is not acceptable for a commercial process. It is also known to decarboxylate a urethane to produce 4-NDPA. See U.S. Pat. No. 3,847,990. However, such method is not commercially practical in terms of cost and yield.

It is known to prepare 4-ADPA by hydrogenating p-nitrosodiphenylhydroxylamine which can be prepared by catalytic dimerization of nitrosobenzene utilizing, as a reducing agent, aliphatic compounds, benzene, naphthalene or ethylenically unsaturated compounds. See, for example, U.S. Pat. Nos. 4,178,315 and 4,404,401. It is also known to prepare p-nitrosodiphenylamine from diphenylamine and an alkyl nitrate in the presence of excess hydrogen chloride. See, for example, U.S. Pat. Nos. 4,518,803 and 4,479,008.

Aromatic amide bonds are currently formed by the reaction of an amine with an acid chloride. This method of forming aromatic amide bonds is also disadvantageous in that chloride is displaced which is corrosive to the reactors, and appears in the waste stream from which it must be removed at considerable expense. A nonhalide process which produces aromatic amide bonds in the substituted aromatic amines would eliminate these problems.

The process of the invention is a nonhalide process for preparing substituted aromatic amines and therefore eliminates the expensive halide removal from the waste stream as well as corrosion problems caused by the halide. In addition, substituted aromatic amines containing aromatic amide bonds can be prepared by the process of the invention.

SUMMARY OF THE INVENTION

It is an object of the invention to provide a process for producing substituted aromatic amines for use in preparing alkylated aromatic amines or substituted derivatives thereof. It is a further object of the invention to provide a process for producing 4-ADPA or substituted derivatives thereof for use in preparing alkylated p-phenylenediamines or substituted derivatives thereof. It is a further object of the invention to provide an efficient and economical process to produce 4-ADPA or substituted derivatives thereof and alkylated p-phenylenediamines that is commercially viable. It is a still further object of the invention to provide a process for producing alkylated p-phenylenediamines or substituted derivatives thereof for use as antioxidants and antiozonants.

According to the invention, a process for preparing substituted aromatic amines is provided which comprises contacting a nucleophilic compound selected from the group consisting of aniline, substituted aniline derivatives, aliphatic amines, substituted aliphatic amine derivatives and amides with an azo containing compound represented by the formula $X-R_1-N=N-R_2-Y$ or azoxy or hydrazo derivatives thereof in the presence of a suitable solvent system, and reacting the nucleophilic compound and a compound represented by the formula $X-R_1-N=N-R_2-Y$ or azoxy or hydrazo derivatives thereof in the presence of a suitable base and a controlled amount of protic material at a reaction temperature of about 10° C. to about 150° C. in a confined reaction zone, wherein the molar ratio of protic material to base is 0:1 to about 5:1, wherein $R_1$ is an aromatic group and $R_2$ is selected from the group consisting of aliphatic and aromatic groups, and X and Y are independently selected from the group consisting of hydrogen, halides, $-NO_2$, $-NH_2$, aryl groups, alkyl groups, alkoxy groups, sulfonate groups, $-SO_3H$, $-OH$, $-COH$, $-COOH$, and alkyl, aryl, arylalkyl or alkylaryl groups containing at least one $-NH_2$ group and reducing the product of the reaction of the nucleophilic compound and the azo containing compound under conditions which produce the substituted aromatic amine. When $R_2$ is an aliphatic group, X is in the meta or ortho position on $R_1$. When $R_2$ is an aromatic group, at least one of X and Y is in the meta or ortho position on $R_1$ and R2, respectively. Halides are selected from the group consisting of chloride, bromide and fluoride. Sulfonate groups, as used herein, are the esters of sulfonic acids. Examples of sulfonates include, but are not limited to, alkyl sulfonates, aralkyl sulfonates, aryl sulfonates, and the like.

In one embodiment, a process for preparing 4-aminodiphenylamine or substituted derivatives thereof is provided which comprises contacting aniline or substituted aniline derivatives and azobenzene or substituted azobenzene derivatives or azoxy or hydrazo derivatives thereof in the presence of a suitable solvent system, and reacting the aniline or substituted aniline derivatives and azobenzene or substituted azobenzene derivatives in the presence of a suitable base and a controlled amount of protic material at a suitable reaction temperature of about 10° C. to about 150° C. in a confined reaction zone wherein the molar ratio of protic material to base is 0:1 to about 5:1, and reducing the product of the reaction of the aniline or substituted derivative thereof and the azobenzene or substituted derivative thereof under conditions which produce the 4-aminodiphenylamine or substituted derivative thereof.

Further according to the invention, a process for preparing an alkylated aromatic amine or substituted derivatives thereof is provided which comprises reductively alkylating the substituted aromatic amines prepared according to the invention.

DETAILED DESCRIPTION OF THE INVENTION

This invention relates to a process for preparing substituted aromatic amines comprising:
  (a) contacting a nucleophilic compound selected from the group consisting of aniline, substituted aniline derivatives, aliphatic amines, substituted aliphatic amine derivatives and amides and an azo containing compound represented by the formula X—$R_1$—N=N—$R_2$—Y or azoxy or hydrazo derivatives thereof in the presence of a suitable solvent system, and
  (b) reacting a nucleophilic compound selected from the group consisting of aniline, substituted aniline derivatives, aliphatic amines, substituted aliphatic amine derivatives and amides and an azo containing compound represented by the formula X—$R_1$—N=N—$R_2$—Y or azoxy or hydrazo derivatives thereof in the presence of a suitable base and a controlled amount of protic material at a reaction temperature of about 10° C. to about 150° C. in a confined reaction zone, wherein the molar ratio of protic material to base is 0:1 to about 5:1, wherein $R_1$ is an aromatic group, $R_2$ is selected from the group consisting of aliphatic and aromatic groups, and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, and alkyl, aryl, arylalkyl or alkylaryl groups containing at least one —$NH_2$ group, wherein if $R_2$ is aliphatic, X is in the meta or ortho position on $R_1$, and if $R_2$ is aromatic, at least one of X and Y is in the meta or ortho position on $R_1$ and $R_2$, respectively, and wherein halides are selected from the group consisting of chloride, bromide and fluoride, and
  (c) reducing the reaction product of (b) under conditions which produce the substituted aromatic amine.

For producing alkylated aromatic amines or substituted derivatives thereof, the process of the invention further comprises:
  (d) reductively alkylating the substituted aromatic amines.

For producing substituted aromatic amines when the nucleophilic compound is an amide, the process of the invention further comprises:
  (d') reacting the substituted aromatic amine with ammonia under conditions which produce the corresponding substituted aromatic amine and amide.

Alternatively, for producing substituted aromatic amines when the nucleophilic compound is an amide, the process of the invention further comprises:

(d') reacting the substituted aromatic amine with water in the presence of a suitable basic or acidic catalyst under conditions which produce the corresponding substituted aromatic amine and the acid or salt thereof corresponding to the amide of (a).

The substituted aromatic amines prepared according to step (d') can be reductively alkylated to produce the corresponding alkylated aromatic amine.

In one embodiment, this invention relates to a process for preparing 4-ADPA or substituted derivatives thereof comprising:
  (a) contacting aniline or substituted aniline derivatives and azobenzene or substituted azobenzene derivatives or azoxy or hydrazo derivatives thereof in the presence of a suitable solvent system, and
  (b) reacting the aniline or substituted aniline derivatives and azobenzene or substituted azobenzene derivatives or azoxy or hydrazo derivatives thereof in the presence of a suitable base and a controlled amount of protic material at a reaction temperature of about 10° C. to about 150° C. in a confined reaction zone wherein the molar ratio of protic material to base is 0:1 to about 5:1, and
  (c) reducing the reaction product of (b) under conditions which produce the 4-ADPA or substituted derivatives thereof.

For producing alkylated p-phenylenediamines or substituted derivative thereof, the process of the invention further comprises:
  (d) reductively alkylating the 4-ADPA or substituted derivatives thereof.

This invention further relates to a process for preparing an alkylated aromatic amine or substituted derivative thereof comprising:
  (a) contacting a nucleophilic compound selected from the group consisting of aniline, substituted aniline derivatives, aliphatic amines, substituted aliphatic amine derivatives and amides, and an azo containing compound represented by the formula X—$R_1$—N=N—$R_2$—Y or azoxy or hydrazo derivatives thereof in the presence of a suitable solvent system, and
  (b) reacting the nucleophilic compound and azo containing compound in the presence of a suitable base and a controlled amount of protic material at a reaction temperature of from about 10° C. to about 150° C. in a confined reaction zone wherein the molar ratio of protic material to base is 0:1 to about 5:1, wherein $R_1$ is an aromatic group, $R_2$ is selected from the group consisting of aliphatic and aromatic groups, and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, and alkyl, aryl, arylalkyl or alkylaryl groups containing at least one —$NH_2$ group wherein if $R_2$ is aliphatic, X is in the meta or ortho position on $R_1$ and if $R_2$ is aromatic, at least one of X and Y is in the meta or ortho position on $R_1$ and R2, respectively, and wherein halides are selected from the group consisting of chloride, bromide and fluoride to produce a substituted aromatic azo compound, and
  (c) reductively alkylating the reaction product of (b) under conditions which produce the alkylated aromatic amine or substituted derivative thereof.

For producing alkylated aromatic amines when the nucleophilic compound is an amide, the process of the invention further comprises:

(d) reacting the alkylated aromatic amine or substituted derivative thereof with ammonia under conditions which produce the corresponding alkylated aromatic amine or substituted derivative thereof and amide.

For producing alkylated aromatic amines when the nucleophilic compound is an amide, the process of the invention can alternatively comprise reacting the substituted aromatic azo compound of step (b) with ammonia under conditions which produce the corresponding substituted aromatic azo compound and amide prior to the reductive alkylation of step (c).

Alternatively, for producing alkylated aromatic amines when the nucleophilic compound is an amide, the process of the invention further comprises:

(d) reacting the alkylated aromatic amine or substituted derivative thereof with water in the presence of a suitable basic or acidic catalyst under conditions which produce the corresponding alkylated aromatic amine or substituted derivative thereof and the acid or salt thereof corresponding to the amide of (a).

For producing alkylated aromatic amines when the nucleophilic compound is an amide, the process of the invention can alternatively comprise reacting the substituted aromatic azo compound of step (b) with water in the presence of a suitable basic or acidic catalyst under conditions which produce the corresponding substituted aromatic azo compound and the acid or salt thereof corresponding to the amide of (a) prior to the reductive alkylation of step (c).

In the preparation of substituted aromatic azo compounds, the molar ratio of a nucleophilic compound selected from the group consisting of aniline, substituted aniline derivatives, aliphatic amines, substituted aliphatic amine derivatives and amides to $X-R_1-N=N-R_2-Y$ or azoxy or hydrazo derivatives thereof can vary from a large excess of $X-R_1-N=N-R_2-Y$ or azoxy or hydrazo derivatives thereof to a large excess of a nucleophilic compound selected from the group consisting of aniline, substituted aniline derivatives, aliphatic amines, substituted aliphatic amine derivatives and amides. Preferably, the reaction is conducted utilizing an excess of a nucleophilic compound selected from the group consisting of aniline, substituted aniline derivatives, aliphatic amines, substituted aliphatic amine derivatives and amides. More preferably, the molar ratio of nucleophilic compound to $X-R_1-N=N-R_2-Y$ or azoxy or hydrazo derivatives thereof is at least about 1:1.

As used herein, the term "substituted aniline derivatives" means aniline containing one or more electron withdrawing or electron releasing substituents on the aromatic ring. Applicable substituents include, but are not limited to, halides, $-NO_2$, $-NH_2$, alkyl groups, alkoxy groups, sulfonate groups, $-SO_3H$, $-OH$, $-COOH$ and aryl, arylalkyl or alkylaryl groups containing at least 1 $-NH_2$ group. Halides are selected from the group consisting of chloride, bromide or fluoride. The preferred alkyl and alkoxy groups contain from 1 to about 6 carbon atoms. The preferred aryl, arylalkyl and alkylaryl groups contain from about 6 to about 18 carbon atoms. Examples of substituted aniline derivatives include, but are not limited to, 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylenediamine, 4,4'-methylenedianiline, 1,3,5-triaminobenzene and mixtures thereof.

Aniline or substituted aniline derivatives can be added directly or can be formed in situ by addition of a compound that will form aniline or the corresponding aniline derivative under the conditions present in the reaction system.

Amides that can be employed according to the invention include aromatic amides, aliphatic amides, substituted aromatic amide derivatives, substituted aliphatic amide derivatives and diamides having the formula:

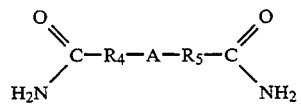

wherein $R_4$ and $R_5$ are independently selected from the group consisting of aromatic groups, aliphatic groups and a direct bond, and A is selected from the group consisting of

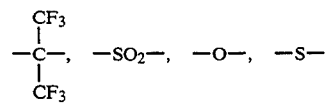

and a direct bond.

The aliphatic amides and substituted aliphatic amide derivatives that can be employed according to the invention are represented by the formula:

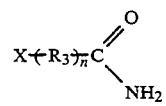

wherein n is 0 or 1, $R_3$ is selected from the group consisting of alkyl, arylalkyl, alkenyl, arylalkenyl, cycloalkyl and cycloalkenyl groups and X is selected from the group consisting of hydrogen, $-NO_2$, $-NH_2$, aryl groups, alkoxy groups, sulfonate groups, $-SO_3H$, $-OH$, $-COH$, $-COOH$, and alkyl, aryl, arylalkyl or alkyl aryl groups containing at least one $-NH_2$ group. The preferred alkyl and alkoxy groups contain from 1 to about 6 carbon atoms. The preferred aryl, arylalkyl and alkyl aryl groups contain from about 6 to about 18 carbon atoms.

Examples of aliphatic amides and substituted aliphatic amide derivatives include, but are not limited to, isobutyramide, urea, acetamide, propylamide and mixtures thereof.

As used herein, the term "substituted aromatic amide derivatives" means aromatic amides containing one or more electron withdrawing or electron releasing substituents on the aromatic ring. Applicable substituents include, but are not limited to, halides, $-NO_2$, $-NH_2$, alkyl groups, alkoxy groups, sulfonate groups, $-SO_3H$, $-OH$, $-COH$, $-COOH$, and alkyl, aryl, arylalkyl or alkyl- aryl groups containing at least one $-NH_2$ group. Halides are selected from the group consisting of chloride, bromide and fluoride. The preferred alkyl and alkoxy groups contain from 1 to about 6 carbon atoms. The preferred aryl, arylalkyl and alkyl aryl groups contain from about 6 to about 18 carbon atoms.

Examples of aromatic amides and substituted aromatic amide derivatives include, but are not limited to, benzamide, 4-methylbenzamide, 4-methoxybenzamide, 4-chlorobenzamide, 2-methylbenzamide, 4-nitrobenzamide, 4-aminobenzamide and mixtures thereof.

Diamides that can be employed according to the process of the invention include, but are not limited to, adipamide, oxalic amide, terephthalic diamide, 4,4'-biphenyldicarboxamide and mixtures thereof.

Aliphatic amines and substituted aliphatic amines that can be employed according to the invention are compounds selected from the group consisting of compounds represented by the formula $X'—R_6—NH—R_7—Y'$ and compounds represented by the formula:

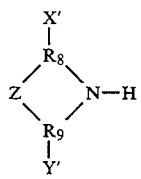

wherein $R_6$ is selected from the group consisting of alkyl, alkenyl, cycloalkyl and cycloalkenyl groups, $R_7$ is selected from the group consisting of a direct bond, alkyl, alkenyl, cycloalkyl and cycloalkenyl groups, $R_8$ and $R_9$ are independently selected from the group consisting of alkyl and alkenyl groups, Z is selected from the group consisting of a direct bond, $—NH—$, $—N(R_{10})—$, $—O—$ and $—S—$, wherein $R_{10}$ is an alkyl group, and $X'$ and $Y'$ are independently selected from the group consisting of hydrogen, halides, $—NO_2$, $—NH_2$, aryl groups, alkoxy groups, sulfonate groups, $—SO_3H$, $—OH$, $—COH$, $—COOH$, and alkyl, aryl, arylalkyl or alkylaryl groups containing at least one $—NH_2$ group. Halides are selected from the group consisting of chloride, bromide and fluoride. The preferred aliphatic groups of $R_6$ and $R_7$ contain from 1 to about 12 carbon atoms. The preferred aryl, arylalkyl and alkylaryl groups contain from about 6 to about 18 carbon atoms. The preferred alkoxy groups contain from 1 to about 6 carbon atoms.

Examples of aliphatic amines and substituted aliphatic amine derivatives include, but are not limited to, cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, hexamethylene diamine, 2-amino-1-propanol, 2-amino-1-butanol, 6-aminohexanoic acid and mixtures thereof.

As used herein, the term "azo containing compounds" are compounds of the invention that are represented by the formula $X—R_1—N=N—R_2—Y$ or azoxy or hydrazo derivatives thereof wherein $R_1$ is an aromatic group, $R_2$ is selected from the group consisting of aliphatic and aromatic groups and X and Y are independently selected from the group consisting of hydrogen, halides, $—NO_2$, $—NH_2$, aryl groups, alkyl groups, alkoxy groups, sulfonate groups, $—SO_3H$, $—OH$, $—COH$, $—COOH$, and alkyl, aryl, arylalkyl or alkylaryl groups containing at least one $—NH_2$ group. When $R_2$ is an aliphatic group, X is in the meta or ortho position on $R_1$. When $R_2$ is aromatic, at least one of X and Y is in the meta or ortho position on R1 and $R_2$, respectively. Halides are selected from the group consisting of chloride, bromide and fluoride. The preferred aliphatic groups of $R_1$ and $R_2$ contain from 1 to about 12 carbon atoms and the preferred aromatic groups of $R_1$ and $R_2$ contain from about 6 to about 18 carbon atoms. The preferred alkyl and alkoxy groups contain from 1 to about 6 carbon atoms. The preferred aryl, arylalkyl and alkylaryl groups contain from about 6 to about 18 carbon atoms. Examples of azo containing compounds include, but are not limited to, azobenzene, substituted azobenzene derivative, azoxybenzene, 4-(phenylazo)diphenylamine, 1,2-diphenylhydrazine, and mixtures thereof.

When the azo containing compound is azobenzene, azobenzene can be produced via the oxidative coupling of aniline in the presence of a suitable base. When the nucleophilic compound used to react with azobenzene is aniline and the reaction is conducted under aerobic conditions, the azobenzene can be produced in-situ via the oxidative coupling of aniline in the presence of a suitable base. The oxidative coupling of aniline is known in the art, see Jeon, S. and Sawyer, D. T., "Hydroxide-Induced Synthesis of the Superoxide Ion From Dioxygen and Aniline, Hydroxylamine, or Hydrazine", Inorg. Chem., 1990, Vol. 29, pp. 4612–15, and the reaction conditions defined herein for the production of the substituted aromatic azo compounds are sufficient for the oxidative coupling of aniline to azobenzene.

As used herein, the term "substituted azobenzene derivatives" means azobenzene containing one or more electron withdrawing or electron releasing substituents on one or both of the aromatic rings. Applicable substituents include, but are not limited to, halides, $—NO_2$, $—NH_2$, alkyl groups, alkoxy groups, sulfonate groups, $—SO_3H$, $—OH$, $—COOH$ and aryl, arylalkyl or alkylaryl groups containing at least one $—NH_2$ group. Halides are selected from the group consisting of chloride, bromide and fluoride. The preferred alkyl and alkoxy groups contain from 1 to about 6 carbon atoms. The preferred aryl, arylalkyl, and alkylaryl groups contain from about 6 to about 18 carbon atoms. Examples of substituted azobenzene derivatives include, but are not limited to, 3,4'-dichloroazobenzene, p-phenylazobenzene sulfonic acid, p-(2,4dihydroxyphenylazo)benzene sulfonic acid, and mixtures thereof.

Suitable solvent systems include, but are not limited to, solvents such as dimethylsulfoxide, nucleophilic compounds such as substituted aniline derivatives, aniline and amides having a melting point below the reaction temperature, e.g., molten benzamide, dimethylformamide, N-methyl-2-pyrrolidone, pyridine, ethyleneglycoldimethyl ether, amines such as diisopropylethylamine, sec-butyl amine and 2-heptylamine, and the like, and mixtures thereof. As described in more detail below, solvent mixtures can be utilized wherein in one or more of the suitable solvents and another solvent, such as a controlled amount of a protic solvent, e.g., methanol or water, are combined.

Suitable bases include, but are not limited to, organic and inorganic bases such as alkali metals, such as sodium metal, alkali metal hydrides, hydroxides and alkoxides, such as sodium hydride, lithium hydroxide, sodium hydroxide, cesium hydroxide, potassium hydroxide, potassium t-butoxide, and the like, including mixtures thereof. Other acceptable base materials include, but are not limited to, phase transfer catalysts in conjunction with a suitable base source such as tetrasubstituted ammonium hydroxides or halides wherein each substituent is independently selected from alkyl, aryl or arylalkyl groups wherein the alkyl, aryl and arylalkyl groups preferably have 1 to about 18 carbon atoms, including tetraalkyl ammonium hydroxides, e.g., tetramethylammonium hydroxide, tetraalkylammonium halides, e.g., tetrabutylammonium chloride, aryl, trialkylammonium hydroxides, e.g., phenyltrimethylammonium hydroxide, arylalkyl, trialkyl ammonium hydroxides, e.g., benzyltrimethylammonium hydroxide, alkyl substituted diammonium hydroxides, e.g., bis-dibutylethylhexamethylenediammonium hydroxide, and other combinations of phase transfer catalysts and suitable bases such as suitable bases in conjunction with aryl ammonium salts, crown ethers and the like, amine bases such as lithium, bis(trimethylsilyl) amide, 2-aminoheptane, and the like, and alkyl magnesium halides, including mixtures thereof. Preferred materials for use as bases are alkali metal hydroxides, such as potassium hydroxide, alkali metal alkoxides such as potassium t-butoxide, alkali metal hydroxides or alkoxides in conjunction with a phase transfer catalyst such as potassium hydroxide in conjunction with crown ethers, and tetraalkylammonium hydroxides such as tetramethylammonium hydroxide or tetrabutylammonium hydroxide.

Preferably, the base is added to the nucleophilic compound to produce a mixture which is then combined with the azo containing compound or substituted aromatic azo compound. Alternatively, the base can be added after the nucleophilic compound and azo containing compound or substituted aromatic azo compound have been combined. Addition of materials can be above or below surface addition.

For the preparation of substituted aromatic amines, the amount of base employed according to the invention can be conveniently expressed in terms of a molar ratio of suitable base to azo containing compound. Broadly, the molar ratio of base to azo containing compound will be about 1:1 to about 10:1, preferably about 1:1 to about 4:1, and most preferably about 1:1 to about 2:1.

The reaction of the nucleophilic compound with the azo containing compound is conducted at a temperature within the range of from about 10° C. to about 150° C., such as from about 20° C. to about 120° C., preferably from about 30° C. to about 100° C. A most preferred temperature for conducting the reaction of the nucleophilic compound with the azo containing compound is from about 50° C. to about 90° C.

Control of the amount of protic material present in the reaction of the nucleophilic compound with the azo containing compound is important. The amount of protic material employed according to the invention can be conveniently expressed in terms of a molar ratio based on the amount of base present at the beginning of the reaction of nucleophilic compound and azo containing compound. Broadly, the molar ratio of protic material to base will be from 0:1 to about 5:1, preferably from 0:1 to about 3:1, and most preferably 0:1 to about 1:1. Thus, the present reaction could be conducted under anhydrous conditions. As used herein for the reaction of nucleophilic compound and azo containing compound, the term "controlled amount" of protic material is an amount up to that which inhibits the reaction of nucleophilic compound with azo containing compound. The upper limit for the amount of protic material present in the reaction varies with the solvent. In addition, the amount of protic material tolerated will vary with the type of base, amount of base, and base cation, used in the various solvent systems. However, it is within the skill of one in the art, utilizing the teachings of the present invention, to determine the specific upper limit of the amount of protic material for a specific solvent, type and amount of base, base cation and the like. The minimum amount of protic material necessary to maintain selectivity of the desired products will also depend upon the solvent, type and amount of base, base cation and the like, that is utilized and can also be determined by one skilled in the art.

Since the amount of protic material present in the reaction is important, it is possible to reduce the amount of protic material present as much as possible and then add back to the reaction the desired amount. Protic materials that can be utilized to add back to the reaction are known to those skilled in the art and include, but are not limited to, water, methanol, isoamyl alcohol, t-butanol and the like, and mixtures thereof. Methods for measuring the amount of protic material and for reducing the amount of protic material as much as possible are well known in the art. For example, the amount of water present in certain reagents can be determined by utilizing a Karl-Fischer apparatus, and the amount of water can be reduced through distillation and/or drying under reduced pressure, drying in the presence of $P_2O_5$ and other agents, azeotropic distillation utilizing, for example, xylene, and the like, including combinations thereof.

In one embodiment for controlling the amount of protic material during the reaction of nucleophilic compound with azo containing compound, a desiccant is added so as to be present during the reaction of nucleophilic compound with azo containing compound. For example, when the protic material is water, the desiccant removes water present during the reaction of nucleophilic compound and azo containing compound and results in higher conversion of azo containing compound and yields of substituted aromatic azo compound or substituted aromatic amine. As used herein, desiccant is a compound present during the reaction of nucleophilic compound and azo containing compound in addition to the suitable base used. Examples of suitable desiccants include, but are not limited to, anhydrous sodium sulfate, molecular sieves, such as types 4A, 5A, and 13X available from the Union Carbide Corporation, calcium chloride, tetramethylammonium hydroxide dihydrate, anhydrous bases such as KOH and NaOH, and activated alumina.

In another embodiment for controlling the amount of protic material during the reaction of nucleophilic compound and azo containing compound, protic material is continuously removed from the reaction mixture by distillation. If the protic material present forms an azeotrope with one of the compounds in the reaction mixture, the protic material can be removed by continuous azeotropic distillation of protic material utilizing the azeotrope. The continuous removal of protic material allows the use of lower amounts of base in the reaction of nucleophilic compound and azo containing compound while achieving very high conversion of azo containing compound and excellent yields of substituted aromatic azo compound or substituted aromatic amine.

Generally, the reactions can be conducted under aerobic or anaerobic conditions. When the nucleophilic compound is a secondary aliphatic amine, the reactions can be conducted only under aerobic conditions, i.e., under anaerobic conditions the only applicable aliphatic amines or substituted aliphatic amine derivatives are those having the formula $X'—R_6—NH_2$. Under aerobic conditions the reaction is conducted essentially as described above in the reaction zone which is exposed to oxygen, usually by exposure to air. Under aerobic conditions, the pressure at which the reaction is conducted can vary and the optimal pressure, as well as the optimal combination of pressure and temperature, are easily determined by one skilled in the art. For example, the reaction can be conducted at a pressure ranging from about 0 psig (0 kg/cm$^2$) to about 250 psig (17.6 kg/cm$^2$), such as from about 14 psig (1 kg/cm$^2$) to about 150 psig (10.5 kg/cm$_2$). Under anaerobic conditions, the reactions can be conducted at atmospheric pressure or reduced or elevated pressures, in the presence of an inert gas such as, for example, nitrogen or argon. Optimal conditions for a particular set of reaction parameters, such as temperature, base, solvent and the like, are easily determined by one skilled in the art utilizing the teaching of the present invention.

The reduction of substituted aromatic azo compounds to substituted aromatic amines according to the process of the invention can be carried out via a catalytic hydrogenation or via conventional reductive processes. Examples of conventional reductive processes include the use of a hydride source, e.g., sodium borohydride, in conjunction with a suitable catalyst such as a palladium- or platinum-on-carbon catalyst, and the use of zinc dust in conjunction with acetic acid. Preferably, this reduction is conducted by a catalytic reduction wherein hydrogenation is effected under hydrogen pressure in the presence of a suitable hydrogenation catalyst. Examples of suitable metal hydrogenation catalysts include nickel, palladium, platinum, rhodium and the like. The preferred hydrogenation catalysts include platinum-on-carbon, palladium-on-carbon and Raney nickel. The hydrogenation can be conducted in a variety of solvents, such as those solvents used during the reaction of the nucleophilic compound with the azo containing compound. Examples of suitable hydrogenation solvents include, but are not limited to, toluene, xylene, aniline, ethanol, dimethylsulfoxide, water and mixtures thereof. Preferably, the hydrogenation is conducted utilizing a platinum-on-carbon or palladium-on-carbon catalyst in a suitable solvent such as, for example, either ethanol, aniline, or dimethylsulfoxide, mixtures thereof or mixtures which include water as the solvent. When a catalytic hydrogenation is used, the hydrogen pressure will be from about 30 psig (2.1 kg/cm$^2$) H$_2$ to about 2500 psig (176 kg/cm$^2$) H$_2$, preferably about 50 psig (3.5 kg/cm$^2$) H$_2$ to about 340 psig (23.9 kg/cm$^2$) H$_2$. The temperature of the catalytic hydrogenation will be from about 50° C. to about 150° C., preferably about 70° C. to about 120° C. The time required for the catalytic hydrogenation will generally range from about 30 minutes to about 24 hours, preferably about 2 hours to about 12 hours. In the case of reduction utilizing zinc dust and acetic acid, the temperature of the reduction can be as low as ambient temperature.

Reductive alkylation of substituted aromatic amines, e.g., 4-ADPA, or substituted aromatic azo compounds to produce alkylated aromatic amines or substituted derivatives thereof useful as antioxidants or antiozanants can be conducted by any of several well-known methods. See, for example, U.S. Pat. No. 4,900,868. Preferably, the substituted aromatic amine or substituted aromatic azo compound and a suitable ketone or aldehyde are reacted in the presence of hydrogen and a suitable catalyst. Suitable catalysts include nickel, palladium, platinum and rhodium metal catalysts. The preferred catalysts are platinum and palladium catalysts such as platinum-on-carbon and palladium-on-carbon catalysts. Suitable ketones include, but are not limited to, methyl isobutyl ketone (MIBK), acetone, methylisoamyl ketone and 2-octanone. The reaction conditions for the reductive alkylation can be the same as the reduction reaction conditions described above. It should be noted that reduction of substituted aromatic azo compounds and alkylation of the reduced material can be conducted in the same reaction vessel utilizing the ketone as a solvent. See, for example, U.S. Pat. Nos. 3,414,616, 4,463,191, and Bannerjee et al, *J. Chem. Soc. Chem. Comm.*, Vol. 18, pp. 1275–76 (1988). In the embodiment where the nucleophilic compound is an amide and the aminolysis or hydrolysis is conducted after reductive alkylation, a second reductive alkylation can be conducted to produce a dialkylated product.

Aminolysis of substituted aromatic amines or alkylated substituted aromatic amines containing an aromatic amide bond, which can be prepared by reacting an amide as the nucleophilic compound and an azo containing compound to produce a substituted aromatic azo compound followed by reducing or reductively alkylating the substituted aromatic azo compound, can be conducted by reacting the substituted aromatic amine or alkylated substituted aromatic amine with ammonia to produce the corresponding substituted aromatic amine or alkylated substituted aromatic amine and an amide which can be recycled. See for example, Jencks, W. P., *J. Am. Chem. Soc.*, Vol. 92, pp. 3201–3202 (1970). The ammonia can be utilized in the aminolysis reaction as either ammonia or a mixture of ammonia and ammonium hydroxide. If ammonium hydroxide is present, the reaction can produce the acid corresponding to the amide starting material in addition to the amide starting material. Preferably, the substituted aromatic amine containing an aromatic amide bond is reacted with ammonia in the presence of a solvent, e.g., methanol. In addition, aminolysis of substituted aromatic azo compounds containing an aromatic amide bond, which can be prepared by reacting an amide as the nucleophilic compound and an azo containing compound, can be conducted by reacting the substituted aromatic azo compound with ammonia to produce the corresponding substituted aromatic azo compound and amide prior to reducing or reductively alkylating the substituted aromatic azo compound.

Hydrolysis of substituted aromatic amines or alkylated substituted aromatic amines containing an aromatic amide bond, which can be prepared by reacting an amide as the nucleophilic compound and an azo containing compound to produce a substituted aromatic azo compound followed by reducing or reductively alkylating the substituted aromatic azo compound, can be conducted by reacting the substituted aromatic amine or alkylated substituted aromatic amine with water in the presence of a suitable basic or acidic catalyst to produce the corresponding substituted aromatic amine or alkylated substituted aromatic amine and the acid or salt thereof corresponding to the amide starting material. In addition, hydrolysis of substituted aromatic azo compounds containing an aromatic amide bond, which can be prepared by reacting an amide as the nucleophilic compound and an azo containing compound, can be conducted by reacting the substituted aromatic azo compound with water in the presence of a suitable basic or acidic catalyst to produce the corresponding substituted aromatic azo compound and the acid or salt thereof corresponding to the amide starting material prior to reducing or reductively alkylating the substituted aromatic azo compound. Examples of suitable basic catalysts include, but are not limited to, alkali metal hydroxides, alkaline earth metal hydroxides, alkali metal alkoxides, tetraalkylammonium hydroxides, ammonium hydroxide, and the like, and mixtures thereof. Examples of suitable acidic catalysts include, but are not limited to, sulfuric acid, hydrochloric acid, nitric acid, phosphoric acid, and the like, and mixtures thereof. It is currently preferred to use a basic catalyst since selected suitable bases used in the reaction of amide and azo containing compound may also be utilized as the basic catalyst in the hydrolysis reaction. The temperature of the hydrolysis reaction will generally be in the range of about 60° C. to about 120° C.

In a preferred embodiment of the invention, the reduction or reductive alkylation is conducted in the presence of water, e.g., water is added to the reaction mixture at the end of the reaction of the nucleophilic compound and the azo-containing compound. The utilization of water during the reduction or reductive alkylation is particularly useful when the suitable base used during the reaction of the nucleophilic compound and the azo-containing compound is water soluble. When the suitable base used is water soluble, the amount of water added will preferably be at least the amount necessary to extract the suitable base from the organic phase.

Contemplated equivalents of the reactants and reagents set forth above are reactants and reagents otherwise corresponding thereto and having the same general properties wherein one or more of the various groups, e.g., —NO$_2$, are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the process of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the process of this invention. In all preparative methods, all starting materials are known or are readily preparable from known starting materials.

EXAMPLES

Materials and Methods: Aniline, aniline derivatives and azobenzene were purchased from Aldrich Chemical, were reagent grade and were used without further purification. Solvents were purchased from Aldrich Chemical and were anhydrous grade. The tetramethylammonium hydroxide was purchased as the pentahydrate.

HPLC Assay: Reverse phase HPLC was used to analyze the reaction mixtures. A 5 μm Beckman/Altex Ultrasphere-ODS (4.6×150 mm) column was employed using a binary gradient pump system.

A Waters 600 series HPLC equipped with a Vydac 201HS54 (4.6×250 mm) column and UV detection at 254 nm was used to monitor all reactions. The external standard method was utilized in all the analysis. Authentic samples of products to be used as standards were prepared by known literature methods.

| Elution Gradient | | |
|---|---|---|
| Time (min.) | % Solvent A (Water) | % Solvent B (40% Methanol in ACN) |
| 0 | 75 | 25 |
| 35 | 20 | 80 |
| 40 | 0 | 100 |
| 45 | 0 | 100 |
| 46 | 75 | 25 |
| 55 | 75 | 25 |

Example 1

This example illustrates the effect of protic material on the production of 4-(phenylazo)diphenylamine from the reaction of aniline and azobenzene in the presence of a base and phase transfer catalyst.

A mixture of aniline (1.25 g), azobenzene (0.45 g), potassium t-butoxide (0.55 g), and 18-crown-6 (0.65 g) was stirred under nitrogen. Variable amounts of water was added to the reaction and the solution was heated to 80° C. for two hours after which time an aliquot was removed and analyzed by HPLC.

TABLE 1

| Mole Ratio Water:t-Butoxide | % Yield 4-(Phenylazo)-diphenylamine |
|---|---|
| 10 | 0 |
| 3 | 1 |
| 1 | 7 |
| 0.5 | 50 |

Example 2

This example illustrates the production of 4-(phenylazo)diphenylamine and substituted derivatives thereof from the reaction of aniline or substituted aniline derivatives and azobenzene.

(a) 10 mmole of azobenzene, 20 mmole of potassium t-butoxide and 10 mmole of 18-crown-6 was stirred in 10 g of aniline under nitrogen at 80° C. for 30 minutes. A weighted aliquot was sampled for HPLC and was found to contain 40% of 4-(phenylazo)diphenylamine, 50% of azobenzene and 10% of hydrazobenzene.

(b) 10 mmole of azobenzene, 20 mmole of potassium t-butoxide and 10 mmole of 18-crown-6 was stirred in 5 g of p-anisidine under nitrogen at 60° C. for 12 hours. 10 ml of 90% methanol was added to homogenize the solution. A weighted aliquot was sampled for HPLC and was found to contain 80% of 4-(4methoxyphenylazo)diphenylamine and 19% of azobenzene.

(c) 10 mmole of azobenzene, 20 mmole of potassium t-butoxide and 10 mmole of 18-crown-6 was stirred in 5 g of p-chloroaniline under nitrogen at 70° C. for 12 hours. 10 ml of 90% methanol was added to homogenize the solution. A weighted aliquot was sampled for HPLC and was found to contain 31% of 4-(4-chlorophenylazo)diphenylamine, 38% of hydrazobenzene and 30% of azobenzene.

(d) 10 mmole of azo benzene, 20 mmole of potassium t-butoxide and 10 mmole of 18-crown-6 was stirred in 5 g of p-toluidine under nitrogen at 80° C. for 12 hours. 10 ml of 90% methanol was added to homogenize the solution. A weighted aliquot was sampled for HPLC and was found to contain 60% of 4-(tolylphenylazo)diphenylamine and 40% of azobenzene.

(e) 10 mmole of azobenzene, 5 g of p-nitroaniline, 20 mmole of potassium t-butoxide and 10 mmole of 18-crown-6 was stirred in 4 ml of DMSO under nitrogen at 100° C. for 72 hours. 10 ml of 90% methanol was added to homogenize the solution. A weighted aliquot was sampled for HPLC and was found to contain 23% of 4-(nitrophenylazo)diphenylamine and 74% of azobenzene.

(f) 10 mmole of azobenzene, 2 g of 1,4-phenylenediamine, 20 mmole of potassium t-butoxide and 10 mmole of 18-crown-6 was stirred in 4 ml of DMSO under nitrogen at 100° C. for 72 hours. 10 ml of 90% methanol was added to homogenize the solution. A weighted aliquot was sampled for HPLC and was found to contain 90% of 4-(aminophenylazo)diphenylamine.

Example 3

This example illustrates the production of 4-(phenylazo)diphenylamine from the reaction of aniline and azobenzene.

75 ml of 25% aqueous tetramethylammonium hydroxide was evaporated to dryness at 60° C./20 mmHg followed by addition of 18.5 gm of azobenzene and 75 ml of aniline. The solution was stirred at 60° C./20 mmHg for 4 hours, approximately 30 ml of aniline was distilled, then 50 ml of water was added. The aniline solution was assayed to contain 99% yield of 4-(phenylazo)diphenylamine and 6% of N-methylaniline by HPLC based on azobenzene.

Example 4

This example illustrates the production of 4-(phenylazo)diphenylamine under aerobic conditions.

A solution of 25% aqueous tetramethylammonium hydroxide (8 mL) was concentrated under vacuum at 75° C. until solid material formed. Azobenzene (1.8 g) and aniline (10 mL) were added and the solution was stirred under the same conditions for 4 hours and then in the presence of air for 12 hours. Analysis of the reaction by HPLC revealed 90% yield of 4-(phenylazo)diphenylamine.

Example 5

This example illustrates the catalytic hydrogenation of 4-(phenylazo)-diphenylamine to 4-ADPA.

To the 4-(phenylazo)-diphenylamine/aniline solution obtained by the coupling of azo benzene and aniline in the presence of tetramethyl ammonium hydroxide, 5 g of 1% platinum-on-carbon was added and hydrogenated at 2000 psig (141 kg/cm$^2$) hydrogen and 120° C. for 2 hours. The solution was allowed to cool to room temperature and the catalyst was filtered off and washed with methanol. A weighted aliquot was sampled and assayed by HPLC and found to give 83% yield of 4-aminodiphenylamine.

Example 6

This example illustrates the production of 4-ADPA from the reaction of aniline and azobenzene to produce 4-(phenylazo)-diphenylamine followed by subsequent catalytic hydrogenation of the reaction mixture.

A solution of 25% aqueous tetramethyl ammonium hydroxide (8 mL) was concentrated under vacuum at 75° C. until solid material formed. Azobenzene (1.8 g) and aniline (10 mL) were added and the solution was stirred under the same conditions for 4 hours and then in the presence of air for 12 hours. Analysis of the reaction mixture by HPLC revealed a 90% yield of 4-(phenylazo)-diphenylamine. Water (10 mL) and 1 g of 1% platinum-on-carbon catalyst was added to the reaction mixture. The solution was transferred to a 300 cc stainless steel autoclave and was hydrogenated under 70 psig (4.9 kg/cm$^2$) hydrogen at 70° C. for 12 hours. Analysis of the organic layer of the reaction mixture revealed a 90% yield of 4-ADPA based on 4-(phenylazo)-diphenylamine.

Example 7

This example illustrates the reduction of 4-(phenylazo)-diphenylamine to 4-ADPA and aniline using zinc dust and acetic acid.

4-(phenylazo)-diphenylamine (0.3 g) was dissolved into 5 mL of ethanol. To the above solution, 0.07 g of zinc dust was added followed by 1 mL of acetic acid. The solution was stirred under nitrogen for 30 minutes at ambient temperature and the solid was subsequently removed by filtration. A weighted aliquot was samples for HPLC analysis and the yield was determined to be 100% of 4-aminodiphenylamine and 100% of aniline based on 4-(phenylazo)-diphenylamine.

That which is claimed is:

1. A process for preparing a substituted aromatic amine comprising:

(a) contacting a nucleophilic compound selected from the group consisting of aniline, substituted aniline derivatives, aliphatic amines, substituted aliphatic amine derivatives and amides, and an azo containing compound represented by the formula X—R$_1$—N=N—R$_2$—Y or azoxy or hydrazo derivatives thereof in the presence of a suitable solvent system, (b) reacting the nucleophilic compound and azo containing compound in the presence of a suitable base and a controlled amount of protic material at a reaction temperature of from about 10° C. to about 150° C. in a confined reaction zone, wherein the molar ratio of protic material to base is 0:1 to about 5:1 wherein R$_1$ is phenylene and R$_2$ is phenylene or

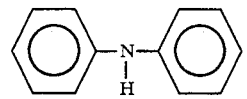

and X and Y are independently selected from the group consisting of hydrogen, halides, —NO$_2$, —NH$_2$, aryl groups, alkyl groups, alkoxy groups, sulfonate groups, —SO$_3$H, —OH, —COH, —COOH, and alkyl, aryl, arylalkyl or alkylaryl groups containing at least one —NH$_2$ group, wherein if R$_2$ is

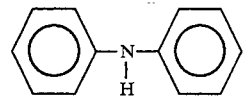

X is in the meta or ortho position on R$_1$ and if R$_2$ is phenylene, at least one of X and Y is in the meta or ortho position on R$_1$ and R$_2$, respectively, and wherein halides are selected from the group consisting of chloride, bromide and fluoride, and (c) reducing the reaction product of (b) under conditions which produce said substituted aromatic amine.

2. The process of claim 1 wherein the reduction of step (c) is a catalytic hydrogenation.

3. The process of claim 2 wherein the catalyst is selected from the group consisting of platinum-on-carbon, palladium-on-carbon and Raney nickel.

4. The process of claim 1 wherein the reduction of step (c) is conducted in the presence of zinc dust and acetic acid.

5. The process of claim 1 wherein water is added to the reaction mixture at the end of step (b).

6. The process of claim 1 wherein the substituent of said substituted aniline derivatives is selected from the group consisting of halides, —NO$_2$, —NH$_2$, alkyl groups, alkoxy groups, sulfonate groups, —SO$_3$H, —OH, —COOH and aryl, arylalkyl or alkylaryl groups containing at least one —NH$_2$ group wherein halides are selected from the group consisting of chloride, bromide and fluoride.

7. The process of claim 6 wherein said substituted aniline derivatives are selected from the group consisting of 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylenediamine, 4,4'-methylene dianiline and 1,4,5-triaminobenzene.

8. The process of claim 1 wherein said nucleophilic compound is an amide and said amide is selected from the group consisting of aromatic amides, aliphatic amides, substituted aromatic amide derivatives, substituted aliphatic amide derivatives and diamides having the formula:

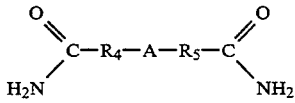

wherein R$_4$ and R$_5$ are independently selected from the group consisting of aromatic groups, aliphatic groups and a direct bond, and A is selected from the group consisting of

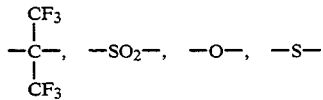

and a direct bond.

9. The process of claim 8 wherein said aliphatic amides and said substituted aliphatic amide derivatives are represented by the formula:

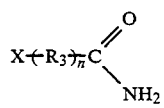

wherein n is 0 or 1, R$_3$ is selected from the group consisting of alkyl, arylalkyl, alkenyl, arylalkenyl, cycloalkyl and cycloalkenyl groups and X is selected from the group consisting of hydrogen, —NO$_2$, —NH$_2$, aryl groups, alkoxy groups, sulfonate groups, —SO$_3$H, —OH, —COH, —COOH, and alkyl, aryl, arylalkyl or alkylaryl groups containing at least one —NH$_2$ group.

10. The process of claim 9 wherein said aliphatic amides and said substituted aliphatic amide derivatives are selected from the group consisting of isobutyramide, urea, acetamide and propyl amide.

11. The process of claim 8 wherein the substituent of said substituted aromatic amide derivatives is selected from the group consisting of halides, —NO$_2$, —NH$_2$, alkyl groups, alkoxy groups, sulfonate groups, —SO$_3$H, —OH, —OH, —COOH and alkyl, aryl, arylalkyl or alkylaryl groups containing at least one —NH$_2$ group, wherein halides are selected from the group consisting of chloride, bromide and fluoride.

12. The process of claim 11 wherein said aromatic amides and said substituted aromatic amide derivatives are selected from the group consisting of benzamide, 4-methylbenzamide, 4-methoxybenzamide, 4-chlorobenzamide, 2-methylbenzamide, 4-nitrobenzamide, and 4-aminobenzamide.

13. The process of claim 8 wherein said diamides are selected from the group consisting of adipamide, oxalic amide, terephthalic diamide, and 4,4'-biphenyldicarboxamide.

14. The process of claim 1 wherein said nucleophilic compound is an aliphatic amine or substituted aliphatic amine derivative and said aliphatic amine and said substituted aliphatic amine derivatives are selected from the group consisting of compounds represented by the formula X'—R$_6$—NH—R$_7$—Y' and compounds represented by the formula:

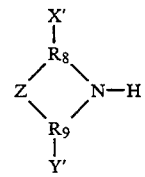

wherein R$_6$ is selected from the group consisting of alkyl, alkenyl, cycloalkyl and cycloalkenyl groups, R$_7$ is selected from the group consisting of a direct bond, alkyl, alkenyl, cycloalkyl and cycloalkenyl groups, R$_8$ and R$_9$ are independently selected from the group consisting of alkyl and alkenyl groups, Z is selected from the group consisting of a direct bond, —NH—, —N(R$_{10}$)—, —O— and —S—, wherein R$_{10}$ is an alkyl group, and X' and Y' are independently selected from the group consisting of hydrogen, halides, —NO$_2$, —NH$_2$, aryl groups, alkoxy groups, sulfonate groups, —SO$_3$H, —OH, —COH, —COOH, and alkyl, aryl, arylalkyl or alkylaryl groups containing at least one —NH$_2$ group, wherein halides are selected from the group consisting of chloride, bromide and fluoride.

15. The process of claim 14 wherein said aliphatic amine and said substituted aliphatic amine derivatives are selected from the group consisting of cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, hexamethylenediamine, 2-amino-1-propanol, 2-amino-1-butanol and 6-aminohexanoic acid.

16. The process of claim 1 wherein said azo containing compounds are selected from the group consisting of azobenzene, azoxybenzene, 4-(phenylazo)-diphenylamine, 3,4'-dichloroazobenzene, p-phenylazobenzene sulfonic acid, p-(2,4-dihydroxyphenylazo)benzene sulfonic acid, and 1,2-diphenylhydrazine.

17. The process of claim 1 wherein said suitable solvent system includes a solvent selected from the group consisting of aniline, dimethylsulfoxide, dimethylformamide, N-methyl-2-pyrrolidone, pyridine, ethyleneglycoldimethyl ether, diisopropylethylamine, molten benzamide and mixtures thereof.

18. The process of claim 17 wherein said suitable solvent system includes a protic solvent.

19. The process of claim 1 wherein the molar ratio of said protic material to said suitable base is 0:1 to about 3:1 and the molar ratio of said suitable base to said azo containing compound is about 1:1 to about 10:1.

20. The process of claim 1 wherein said suitable base is selected from the group consisting of organic and inorganic bases.

21. The process of claim 20 wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides, and mixtures thereof.

22. The process of claim 1 wherein said base is selected from the group consisting of an arylammonium, alkylammonium, aryl/alkylammonium and alkyldiammonium salt in conjunction with a base source.

23. The process of claim 1 wherein said nucleophilic compound is aniline or benzamide and said azo containing compound is azobenzene.

24. The process of claim 23 wherein said nucleophilic compound is aniline and wherein said azobenzene introduced in Step (a) is produced by the oxidative coupling of aniline in the presence of a suitable base.

25. The process of claim 23 wherein said nucleophilic compound is aniline and wherein said reaction is conducted under aerobic conditions and azobenzene is produced in-situ by the oxidative coupling of aniline in the presence of a suitable base.

26. The process of claim 23 wherein said solvent is aniline and said base is selected from the group consisting of 18-crown-6 ether in conjunction with potassium hydroxide or potassium t-butoxide, tetraalkylammonium hydroxide and alkyl substituted diammonium hydroxide.

27. The process of claim 1 wherein said nucleophilic compound and said azo containing compound are reacted under aerobic conditions.

28. The process of claim 1 wherein said nucleophilic compound is selected from the group consisting of aniline, substituted aniline derivatives, aliphatic amines or substituted aliphatic amine derivatives having the formula X'—R$_6$—NH$_2$, and amides and said azo containing compound are reacted under anaerobic conditions wherein R$_6$ is selected from the group consisting of alkyl, alkenyl, cycloalkyl and cycloalkenyl groups and X' is selected from the group consisting of hydrogen, halides, —NO$_2$, —NH$_2$, aryl groups, alkoxy groups, sulfonate groups, —SO$_3$H, —OH, —COH, —COOH, and alkyl, aryl, arylalkyl or alkylaryl groups containing at least one —NH$_2$ group wherein halides are selected from the group consisting of chloride, bromide and fluoride.

29. The process of claim 1 wherein a desiccant is present during step (b) to control the amount of protic material present during the reaction of said nucleophilic compound and said azo containing compound.

30. The process of claim 1 wherein the amount of protic material in step (b) is controlled by the continuous distillation of said protic material.

31. The process of claim 1 wherein said nucleophilic compound in step (a) is an amide further comprising:
(d) reacting said substituted aromatic amine with ammonia under conditions which produce the corresponding substituted aromatic amine and amide.

32. The process of claim 31 further comprising:
(e) reductively alkylating the substituted aromatic amine of (d).

33. The process of claim 1 further comprising:
(d) reductively alkylating the substituted aromatic amine of (c).

34. The process of claim 1 wherein said nucleophilic compound in step (a) is an amide further comprising:
(d) reacting said substituted aromatic amine with water in the presence of a suitable basic or acidic catalyst under conditions which produce the corresponding substituted aromatic amine and the acid or salt thereof corresponding to said amide of (a).

35. The process of claim 34 further comprising:
(e) reductively alkylating the substituted aromatic amine of (d).

36. A process for preparing 4-aminodiphenylamine (4-ADPA) or substituted derivatives thereof comprising:
(a) contacting aniline or substituted aniline derivatives and azobenzene or substituted azobenzene derivatives or azoxy or hydrazo derivatives thereof in the presence of a suitable solvent system,
(b) reacting the aniline or substituted aniline derivatives and azobenzene or substituted azobenzene derivatives or azoxy or hydrazo derivatives thereof in the presence of a suitable base and a controlled amount of protic material at a reaction temperature of about 10° C. to about 150° C. in a confined reaction zone, wherein the molar ratio of protic material to base is 0:1 to about 5:1, and
(c) reducing the reaction product of (b) under conditions which produce said 4-ADPA or substituted derivatives thereof.

37. The process of claim 36 further comprising:
(d) reductively alkylating the 4-ADPA or substituted derivative thereof of (c).

38. The process of claim 36 for preparing 4-ADPA comprising:
(a) contacting aniline and azobenzene in the presence of a suitable solvent system,
(b) reacting the aniline and azobenzene in the presence of a suitable base and a controlled amount of protic material at a reaction temperature of about 10° C. to about 150° C. in a confined reaction zone, wherein the molar ratio of protic material to base is 0:1 to about 5:1, and
(c) reducing the product of (b) under conditions which produce said 4-ADPA, wherein said azobenzene introduced in Step (a) is produced by the oxidative coupling of aniline in the presence of a suitable base.

39. The process according to claim 36 for preparing 4-ADPA comprising:
(a) contacting aniline and azobenzene in the presence of a suitable solvent system,
(b) reacting the aniline and azobenzene in the presence of a suitable base and a controlled amount of protic material at a reaction temperature of about 10° C. to about 150° C. in a confined reaction zone, wherein the molar ratio of protic material to base is 0:1 to about 5:1, and (c) reducing the product of (b) under conditions which produce said 4-ADPA, wherein said reaction is conducted under aerobic conditions and azobenzene is produced in-situ by the oxidative coupling of aniline in the presence of a suitable base.

40. A process for preparing an alkylated aromatic amine or substituted derivative thereof comprising:
(a) contacting a nucleophilic compound selected from the group consisting of aniline, substituted aniline derivatives, aliphatic amines, substituted aliphatic amine derivatives and amides, and an azo containing compound represented by the formula X—$R_1$—N=N—$R_2$—Y or azoxy or hydrazo derivatives thereof in the presence of a suitable solvent system,
(b) reacting the nucleophilic compound and azo containing compound in the presence of a suitable base and a controlled amount of protic material at a reaction temperature of from about 10° C. to about 150° C. in a confined reaction zone wherein the molar ratio of protic material to base is 0:1 to about 5:1, wherein $R_1$ is phenylene and $R_2$ is phenylene or,

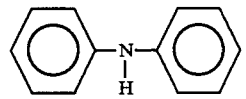

and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, and alkyl, aryl, arylalkyl or alkylaryl groups containing at least one —$NH_2$ group wherein if $R_2$ is,

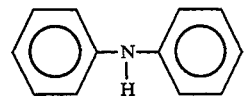

X is in the meta or ortho position on $R_1$ and $R_2$ is phenylene, at least one of X and Y is in the meta or ortho position on $R_1$ and $R_2$, respectively, and wherein halides are selected from the group consisting of chloride, bromide and fluoride to produce a substituted aromatic azo compound, and
(c) reductively alkylating the reaction product of (b) under conditions which produce said alkylated aromatic amine or substituted derivative thereof.

41. The process of claim 40 wherein the reductive alkylation of step (c) is conducted in the presence of a catalyst selected from the group consisting of platinum-on-carbon, palladium-on-carbon and Raney nickel.

42. The process of claim 40 wherein water is added to the reaction mixture at the end of step (b).

43. The process of claim 40 wherein the substituent of said substituted aniline derivatives is selected from the group consisting of halides, —$NO_2$, —$NH_2$, alkyl groups, alkoxy groups, sulfonate groups, —$SO_3H$, —OH, —COOH and aryl, arylalkyl or alkylaryl groups containing at least one —$NH_2$ group wherein halides are selected from the group consisting of chloride, bromide and fluoride.

44. The process of claim 43 wherein said substituted aniline derivatives are selected from the group consisting of 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylenediamine, 4,4'-methylene dianiline and 1,4,5-triaminobenzene.

45. The process of claim 40 wherein said nucleophilic compound is an amide and said amide is selected from the group consisting of aromatic amides, aliphatic amides, substituted aromatic amide derivatives, substituted aliphatic amide derivatives and diamides having the formula:

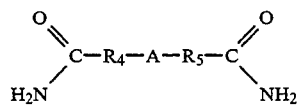

wherein $R_4$ and $R_5$ are independently selected from the group consisting of aromatic groups, aliphatic groups and a direct bond, and A is selected from the group consisting of

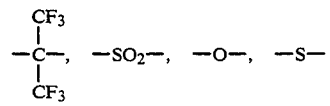

and a direct bond.

46. The process of claim 45 wherein said aliphatic amides and said substituted aliphatic amide derivatives are represented by the formula:

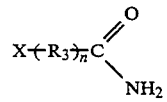

wherein n is 0 or 1, $R_3$ is selected from the group consisting of alkyl, arylalkyl, alkenyl, arylalkenyl, cycloalkyl and cycloalkenyl groups and X is selected from the group consisting of hydrogen, —$NO_2$, —$NH_2$, aryl groups, alkoxy groups, sulfonate groups, —$SO_3H$, —OH, —COH, —COOH, and alkyl, aryl, arylalkyl or alkylaryl groups containing at least one —$NH_2$ group.

47. The process of claim 46 wherein said aliphatic amides and said substituted aliphatic amide derivatives are selected from the group consisting of isobutyramide, urea, acetamide and propyl amide.

48. The process of claim 45 wherein the substituent of said substituted aromatic amide derivatives is selected from the group consisting of halides, —$NO_2$, —$NH_2$, alkyl groups, alkoxy groups, sulfonate groups, —$SO_3H$, —OH, —OH, —COOH and alkyl, aryl, arylalkyl or alkylaryl groups containing at least one —$NH_2$ group, wherein halides are selected from the group consisting of chloride, bromide and fluoride.

49. The process of claim 48 wherein said aromatic amides and said substituted aromatic amide derivatives are selected from the group consisting of benzamide, 4-methylbenzamide, 4-methoxybenzamide, 4-chlorobenzamide, 2-methylbenzamide, 4-nitrobenzamide, and 4-aminobenzamide.

50. The process of claim 45 wherein said diamides are selected from the group consisting of adipamide, oxalic amide, terephthalic diamide, and 4,4'-biphenyldicarboxamide.

51. The process of claim 40 wherein said nucleophilic compound is an aliphatic amine or substituted aliphatic amine derivative and said aliphatic amine and said substituted aliphatic amine derivatives are selected from the group consisting of compounds represented by the formula X'—R$_6$—NH—R$_7$—Y' and compounds represented by the formula:

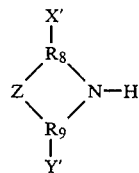

wherein R$_6$ is selected from the group consisting of alkyl, alkenyl, cycloalkyl and cycloalkenyl groups, R$_7$ is selected from the group consisting of a direct bond, alkyl, alkenyl, cycloalkyl and cycloalkenyl groups, R$_8$ and R$_9$ are independently selected from the group consisting of alkyl and alkenyl groups, Z is selected from the group consisting of a direct bond, —NH—, —N(R$_{10}$)—, —O— and —S—, wherein R$_{10}$ is an alkyl group, and X' and Y' are independently selected from the group consisting of hydrogen, halides, —NO$_2$, —NH$_2$, aryl groups, alkoxy groups, sulfonate groups, —SO$_3$H, —OH, —COH, —COOH, and alkyl, aryl, arylalkyl or alkylaryl groups containing at least one —NH$_2$ group, wherein halides are selected from the group consisting of chloride, bromide and fluoride.

52. The process of claim 51 wherein said aliphatic amine and said substituted aliphatic amine derivatives are selected from the group consisting of cyclohexylamine, 2-butylamine, isopropylamine, 2-hexylamine, 2-heptylamine, 1,4-dimethylpentylamine, 1-methylheptylamine, 1-ethyl-3-methylpentylamine, 1,3-dimethylbutylamine, octylamine, piperidine, piperazine, hexamethylenediamine, 2-amino-1-propanol, 2-amino-1-butanol and 6-aminohexanoic acid.

53. The process of claim 40 wherein said azo containing compounds are selected from the group consisting of azobenzene, azoxybenzene, 4-(phenylazo)-diphenylamine, 3,4'-dichloroazobenzene, p-phenylazobenzene sulfonic acid, p-(2,4-dihydroxyphenylazo)benzene sulfonic acid, and 1,2-diphenylhydrazine.

54. The process of claim 40 wherein said suitable solvent system includes a solvent selected from the group consisting of aniline, dimethylsulfoxide, dimethylformamide, N-methyl-2-pyrrolidone, pyridine, ethyleneglycoldimethyl ether, diisopropylethylamine, molten benzamide and mixtures thereof.

55. The process of claim 54 wherein said suitable solvent system includes a protic solvent.

56. The process of claim 40 wherein the molar ratio of said protic material to said suitable base is 0:1 to about 3:1 and the molar ratio of said suitable base to said azo containing compound is about 1:1 to about 10:1.

57. The process of claim 40 wherein said suitable base is selected from the group consisting of organic and inorganic bases.

58. The process of claim 57 wherein said organic and inorganic bases are selected from the group consisting of alkali metals, alkali metal hydrides, alkali metal hydroxides, alkali metal alkoxides, phase transfer catalysts in conjunction with a base source, amines, crown ethers in conjunction with a base source, alkyl magnesium halides, and mixtures thereof.

59. The process of claim 40 wherein said base is selected from the group consisting of an arylammonium, alkylammonium, aryl/alkylammonium and alkyldiammonium salt in conjunction with a base source.

60. The process of claim 40 wherein said nucleophilic compound is aniline or benzamide and said azo containing compound is azobenzene.

61. The process of claim 60 wherein said nucleophilic compound is aniline and wherein said azobenzene introduced in Step (a) is produced by the oxidative coupling of aniline in the presence of a suitable base.

62. The process of claim 60 wherein said nucleophilic compound is aniline and wherein said reaction is conducted under aerobic conditions and azobenzene is produced in-situ by the oxidative coupling of aniline in the presence of a suitable base.

63. The process of claim 60 wherein said solvent is aniline and said base is selected from the group consisting of 18-crown-6 ether in conjunction with potassium hydroxide or potassium t-butoxide, tetraalkylammonium hydroxide and alkyl substituted diammonium hydroxide.

64. The process of claim 40 wherein said nucleophilic compound and said azo containing compound are reacted under aerobic conditions.

65. The process of claim 40 wherein said nucleophilic compound is selected from the group consisting of aniline, substituted aniline derivatives, aliphatic amines or substituted aliphatic amine derivatives having the formula X'—R$_6$—NH$_2$, and amides and said azo containing compound are reacted under anaerobic conditions wherein R$_6$ is selected from the group consisting of alkyl, alkenyl, cycloalkyl and cycloalkenyl groups and X' is selected from the group consisting of hydrogen, halides, —NO$_2$, —NH$_2$, aryl groups, alkoxy groups, sulfonate groups, —SO$_3$H, —OH, —COH, —COOH, and alkyl, aryl, arylalkyl or alkylaryl groups containing at least one —NH$_2$ group wherein halides are selected from the group consisting of chloride, bromide and fluoride.

66. The process of claim 40 wherein a desiccant is present during step (b) to control the amount of protic material present during the reaction of said nucleophilic compound and said azo containing compound.

67. The process of claim 40 wherein the amount of protic material in step (b) is controlled by the continuous distillation of said protic material.

68. The process of claim 40 wherein said nucleophilic compound in step (a) is an amide further comprising:
(d) reacting said alkylated substituted aromatic amine with ammonia under conditions which produce the corresponding alkylated aromatic amine or substituted derivative thereof and amide.

69. The process of claim 68 further comprising:
(c) reductively alkylating the product alkylated aromatic amine or substituted derivative thereof of (d).

70. The process of claim 40 wherein said nucleophilic compound in step (a) is an amide and wherein said substituted aromatic azo compound of step (b) is reacted with ammonia under conditions which produce the corresponding substituted aromatic azo compound and amide prior to the reductive alkylation of step (c).

71. The process of claim 40 wherein said nucleophilic compound in step (a) is an amide further comprising:

(d) reacting said alkylated substituted aromatic amine with water in the presence of a suitable basic or acidic catalyst under conditions which produce the corresponding alkylated aromatic amine or substituted derivative thereof and the acid or salt thereof corresponding to said amide of (a).

72. The process of claim 71 further comprising:
(e) reductively alkylating the product alkylated aromatic amine or substituted derivative thereof of (d).

73. The process of claim 40 wherein said nucleophilic compound in step (a) is an amide and wherein said substituted aromatic azo compound of step (b) is reacted with water in the presence of a suitable basic or acidic catalyst under conditions which produce the corresponding substituted aromatic azo compound and the acid or salt thereof corresponding to said amide of (a) prior to the reductive alkylation of step (c).

74. The process of claim 40 wherein said substituted aromatic azo compound is reductively alkylated utilizing a compound selected from the group consisting of ketones and aldehydes.

75. The process of claim 72 wherein said ketone is selected from the group consisting of acetone, methylisobutylketone, methylisoamylketone and 2-octanone.

76. The process of claim 1 wherein $R_2$ is phenylene.

77. The process of claim 40 wherein $R_2$ is phenylene.

* * * * *